United States Patent [19]

Spears

[11] Patent Number: 5,730,935
[45] Date of Patent: Mar. 24, 1998

[54] HIGH PRESSURE GAS EXCHANGER

[75] Inventor: James Richard Spears, Bloomfield Hills, Mich.

[73] Assignee: Wayne State University, Detroit, Mich.

[21] Appl. No.: 484,284

[22] Filed: Jun. 7, 1995

Related U.S. Application Data

[63] Continuation-in-part of Ser. No. 353,137, Dec. 9, 1994, Pat. No. 5,599,296, which is a continuation-in-part of Ser. No. 273,652, Jul. 12, 1984, Pat. No. 5,569,180, which is a continuation-in-part of Ser. No. 152,589, Nov. 15, 1993, Pat. No. 5,407,426, which is a continuation-in-part of Ser. No. 818,045, Jan. 8, 1992, Pat. No. 5,261,875, which is a continuation of Ser. No. 655,078, Feb. 14, 1991, Pat. No. 5,086,620.

[51] Int. Cl.⁶ .......................... A61M 1/14; A61M 1/34; A61M 37/00
[52] U.S. Cl. .......................... 422/44; 422/45; 422/48; 604/4; 604/24; 604/26; 261/DIG. 28
[58] Field of Search .......................... 422/44, 45, 48; 604/4, 24, 26; 261/DIG. 28

[56] References Cited

U.S. PATENT DOCUMENTS

| | | | |
|---|---|---|---|
| 3,721,231 | 3/1973 | Hubert | 128/2.05 R |
| 4,122,858 | 10/1978 | Schiff | 128/348 |
| 4,205,042 | 5/1980 | Lobdell et al. | 422/47 |
| 4,401,431 | 8/1983 | Arp | 604/4 |
| 4,445,896 | 5/1984 | Gianturco | 604/238 |
| 4,493,692 | 1/1985 | Reed | 604/4 |
| 4,602,987 | 7/1986 | Bonaventura et al. | 205/633 |
| 4,610,661 | 9/1986 | Possis et al. | 604/52 |
| 4,686,085 | 8/1987 | Osterholm | 422/45 |
| 4,834,719 | 5/1989 | Arenas | 604/243 |
| 4,877,031 | 10/1989 | Conway et al. | 128/344 |
| 4,919,895 | 4/1990 | Heldebrant et al. | 422/129 |
| 4,968,483 | 11/1990 | Muller et al. | 422/45 |
| 5,021,044 | 6/1991 | Sharkawy | 604/53 |
| 5,084,011 | 1/1992 | Grady | 604/24 |
| 5,114,423 | 5/1992 | Kasprzyk et al. | 606/27 |
| 5,137,513 | 8/1992 | McInnes et al. | 604/96 |
| 5,158,533 | 10/1992 | Strauss et al. | 604/4 |
| 5,158,540 | 10/1992 | Wijay et al. | 604/43 |
| 5,180,364 | 1/1993 | Ginsburg | 604/53 |

(List continued on next page.)

FOREIGN PATENT DOCUMENTS 2649126   5/1978   Germany.

OTHER PUBLICATIONS

"Use of Hyperbaric Oxygen as Oxygen Source in Extracorporeal Oxygenation of Blood", C. Boe, et al; Physiological And Clinical Aspects of Oxygenator Design, ed. by Dawids and Engell; publ. by Elsevier/North–Holland Biomedical Press, Luxembourg, 1976.

"Cavitation in Gas–Supersaturated Solutions", Edvard A. Hemmingsen; Journal of Applied Physics, vol. 46, No. 1, Jan. 1976.

"Supersaturated Fluorocarbon as an Oxygen Source", Pieter Stroev, et al; Physiological And Clinical Aspects of Oxygenator Design, ed. by Dawids and Engell; publ. by Elsevier/North–Holland Biomedical Press, Luxembourg, 1976.

*Primary Examiner*—Nina Bhat
*Attorney, Agent, or Firm*—Brooks & Kushman P.C.

[57] ABSTRACT

An apparatus 10 and method for delivering a high partial pressure of a gas into a liquid. The apparatus has a gas transfer device 12 with a housing 14 that includes upstream 16 and downstream 18 regions, between which there is located a gas-liquid contacting region 20 with contacting members 22, such as hollow microporous fibers. A reservoir 36 of gas supplies the gas at a high pressure (P) to a flask 38 of gas-depleted liquid and to the gas transfer device 12. The reservoir 36 of gas provides hydrostatic pressure for urging the liquid through the contacting members 22 and propelling the gas around the contacting members 22 so that the gas does not diffuse across the contacting members 22. The gas-enriched liquid is then ducted to a high resistance delivery channel 44 for administration to a site of interest without effervescence, bubble formation, or significant disruption of laminar flow.

14 Claims, 1 Drawing Sheet

U.S. PATENT DOCUMENTS

| | | | |
|---|---|---|---|
| 5,195,971 | 3/1993 | Sirhan | 604/96 |
| 5,211,637 | 5/1993 | Goto et al. | 604/283 |
| 5,226,888 | 7/1993 | Arney | 604/96 |
| 5,252,159 | 10/1993 | Arney | 156/169 |
| 5,273,052 | 12/1993 | Krans et al. | 128/772 |
| 5,279,562 | 1/1994 | Sirhan et al. | 604/96 |
| 5,334,142 | 8/1994 | Paradis | 604/53 |
| 5,356,388 | 10/1994 | Sepetka et al. | 604/164 |
| 5,366,696 | 11/1994 | Williams | 422/45 |
| 5,383,853 | 1/1995 | Jung et al. | 604/96 |
| 5,407,426 | 4/1995 | Spears | 604/24 |
| 5,411,705 | 5/1995 | Thor et al. | 422/45 |
| 5,413,558 | 5/1995 | Paradis | 604/101 |
| 5,437,633 | 8/1995 | Manning | 604/53 |
| 5,569,180 | 10/1996 | Spears | 604/24 |

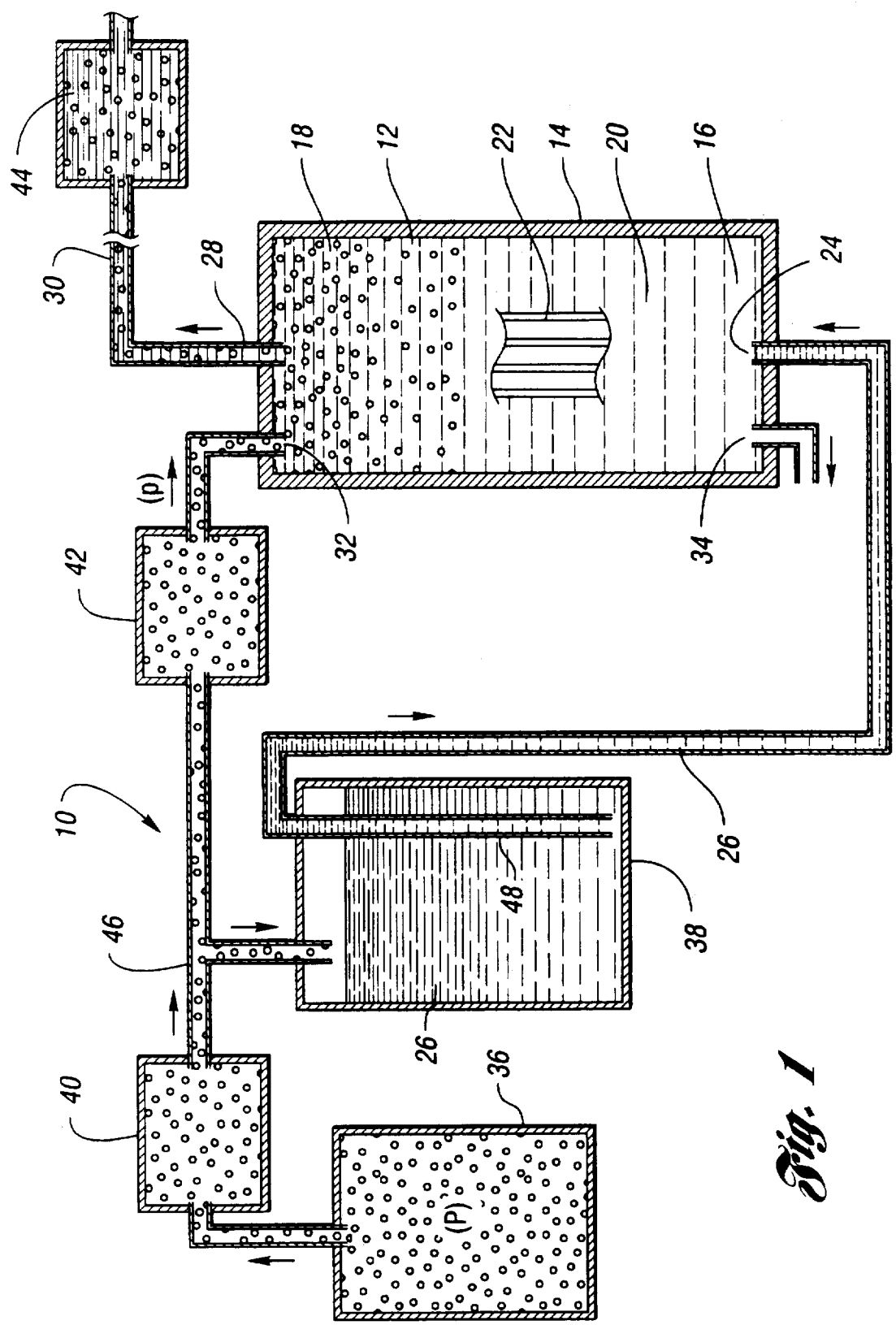

HIGH PRESSURE GAS EXCHANGER

CROSS REFERENCE TO RELATED APPLICATIONS

This application is a continuation-in-part of application Ser. No. 08/353,137, filed on Dec. 9, 1994, now U.S. Pat. No. 5,599,296 which is a continuation-in-part of application Ser. No. 08/273,652, filed Jul. 12, 1994, now U.S. Pat. No. 5,569,180 which is a continuation-in-part of application Ser. No. 08/152,589, filed Nov. 15, 1993 now U.S. Pat. No. 5,407,426, which is a continuation-in-part of application Ser. No. 07/818,045, filed Jan. 8, 1992 now U.S. Pat. No. 5,261,875, which is a continuation of application Ser. No. 07/655,078, filed Feb. 14, 1991 now U.S. Pat. No. 5,086,620. The disclosures in each of the above-referenced cases are incorporated herein by reference.

TECHNICAL FIELD

This invention relates to an apparatus and method for generating a relatively high partial pressure of a gas in liquid by the use of an oxygenator.

BACKGROUND ART

In many industrial and clinical environments, it would be desirable to deliver a gas-enriched fluid to a site of interest. For example, in industrial applications it would be desirable to deliver carbon dioxide rapidly via a liquid transfer medium to a fire in order to extinguish the flame without the carbon dioxide becoming prematurely liberated from its dissolved state in the transfer medium. As another exampled the environmental problems of a toxic site cleanup may be ameliorated if a neutralizing or cleansing gaseous agent is delivered rapidly and at high concentration by a transporting medium into the area which requires cleansing.

In clinical applications, as has been disclosed in my previous patent applications referenced above, it would be highly desirable to treat patients, for example stroke victims, by having ready access to a system which would deliver an oxygen-enriched blood stream rapidly to the anatomical area where the need for oxygen enrichment is most acute.

For simplicity and brevity, the examples discussed below are primarily selected from clinical environments, although the applicability of the concepts and needs to be discussed to non-clinical, including industrial, environments will be apparent to those of skill in the art.

In the clinical area, if oxygen-supersaturated blood prematurely liberates oxygen at the wrong place and at the wrong time, an embolism may result. Its adverse consequences are well-known. For example, the stroke victim may experience a sudden attack of weakness affecting one side of the body as a consequence of an interruption to the flow of blood to the brain. The primary problem may be located in the heart or blood vessels. The effect on the brain is secondary. Blood flow may be prevented by clotting (thrombosis), a detached clot that lodges in an artery (embolus), or by rupture of an artery wall (hemorrhage). In any event, a severe interruption to the rate of mass transfer of oxygen-enriched blood occurs if laminar flow becomes disturbed by bubble formation and its consequent turbulent flow characteristics.

Ideally, the physician should be able to administer an oxygen-enriched, supersaturated blood flow in a laminar fashion quickly to a site of interest without premature liberation of oxygen after it leaves a delivery apparatus, and undergoes a pressure drop before arrival at the site requiring treatment.

What therefore is needed is a method and apparatus available to the physician and industrialist which will enable them to deliver gas-enriched fluids into environments of interest without premature formation of bubbles in the transferring medium.

In the past, the main objections to the clinical use of hyperbaric oxygen have been the risk of hemolysis and bubble emboli, together with the complexity of the equipment. Dawids and Engell, PHYSIOLOGICAL AND CLINICAL ASPECTS OF OXYGENATOR DESIGN, "Proceedings On Advances In Oxygenator Design", June 1975, p. 140, note that attempts to use oxygen at higher pressures call for the blood to be pumped into the high pressure area where it is exposed to the oxygen and then throttled down to normal pressure. These workers note that such operations have caused considerable hemolysis, which is more pronounced as the gas pressure increases. Additionally, bubble formation may occur as a result of a rapid pressure decrease and the high velocities in the throttling region. Id.

SUMMARY OF THE INVENTION

Disclosed is an apparatus and method for delivering a high partial pressure of a gas into a liquid. The apparatus includes a gas transfer device with contacting members in a gas-liquid contacting region thereof.

A reservoir of gas supplies the gas at a high pressure (P) to a flask of gas-depleted liquid. The flask is in liquid communication with the gas transfer device and in gaseous communication therewith at a pressure (p), where p is less than P.

The reservoir of gas provides a single source of hydrostatic pressure for urging the liquid through the contacting members and the gas around the contacting members so the gas does not diffuse across the contacting members.

The advantages of the present invention are readily apparent from the following detailed description of the best mode for carrying out the invention when taken in connection with the accompanying drawings.

BRIEF DESCRIPTION OF THE DRAWINGS

FIG. 1 is a diagrammatic illustration of a representative apparatus in which a relatively high partial pressure of a gas can be achieved in a liquid.

BEST MODE(S) FOR CARRYING OUT THE INVENTION

Turning first to FIG. 1 of the drawing, there is depicted an apparatus 10 for delivering a high partial pressure of a gas into a liquid. The apparatus includes a gas transfer device 12 with a housing 14. Included in the housing is an upstream region 16, a downstream region 18, and a gas-liquid contacting region 20 with contacting members 22, such as microporous hollow fibers, or solid diffusible membranes. The contacting members 22 are located intermediate the upstream 16 and downstream 18 regions.

To receive a supply of liquid, a gas-depleted liquid inlet port 24 is provided in the upstream region 16. A liquid outlet port 28 is defined in the downstream region 18 for delivering gas-enriched liquid to a high resistance delivery channel 44, such as a catheter for medical applications. For industrial applications, a suitable delivery device such as a nozzle or its equivalents may be deployed.

A gas inlet port 32 is defined in the housing 14 for receiving the gas before contact with the liquid in the contacting region 20. Also provided in the housing 14 is a gas outlet port 34 for returning gas which is undissolved in the liquid.

A reservoir 36 of gas supplies the gas at a high pressure (P). In gaseous communication with the reservoir 36 is a flask 38 of gas-depleted liquid. If desired; means could be provided for continuous replenishment of the liquid. As illustrated in FIG. 1, the flask is in liquid communication with the liquid inlet port 24 and via a "T" junction 46 is in gaseous communication with the gas inlet port 32 of the gas transfer device 12. First and second regulators 40, 42 progressively reduce the gas pressure from a value represented by (P) in the flask 38 to a lower pressure (p) upon entry into the gas inlet port 32.

Thus, the disclosed apparatus enables the reservoir 36 of gas to provide a hydrostatic pressure which not only urges the liquid through the contacting members 22, but also urges the gas around the contacting members 22. In this way, the gas does not diffuse across the members, thus promoting mass transfer of the gas into the liquid.

The apparatus of the present invention will now be described in further detail. In one set of experiments, a pediatric hollow fiber (polypropylene) oxygenator (Turumo), which is normally used for oxygenation of venous blood during extracorporeal circulation in children was modified. One of two oxygen ports 32, 34 was connected to a reservoir 36 of oxygen. The partial pressure of the gas was adjusted with the regulator 40. A tubing from the latter was connected to a stainless steel tank 38 (Norris, 27 liter capacity) which had been filled with distilled water.

A liquid conduit section 48 extended below the meniscus of the liquid contained within the flask, which allowed flow of liquid from the bottom of the flask to the liquid in port 24 of the gas transfer device: or oxygenator 12. From a "T" junction 46, a second regulator 42 allowed adjustment of gas pressure to a value (p) that was 5 to 20 psi lower than the input pressure (P).

Tubing leading to the regulator 42 was connected to the gas inlet port 32 of the oxygenator 12.

The arrangement allowed a single tank 36 of oxygen to provide the driving hydrostatic pressure needed to (1) urge water through the interior of the hollow fibers 22 within the oxygenator 12 and (2) cause oxygen to flow around the outside of the bundle of hollow fibers 22.

The pressure difference across each hollow fiber ensured that oxygen did not directly diffuse across the hollow fibers in its gaseous state.

Three different runs performed with a hydrostatic pressure maintained at approximately 45 psi within the hollow fibers and an oxygen gas pressure of about 20 psi showed the same result.

When the effluent from the channel 44 was delivered into ordinary tap water through either a metal or plastic tubing having an internal diameter of approximately 0.5 mm, no bubbles were noted. The $PO_2$ of the effluent was approximately 1800 mm Hg, a value similar to what would be predicted, assuming full equilibration of the gas pressure outside the fibers to that dissolved in water within the fibers.

It should be noted that no additional application of hydrostatic pressure was found to be necessary to prevent bubble formation.

It is likely that, at relatively low dissolved gas partial pressures, on the order of a few bar, the use of filtered water, which had been allowed to stand for many hours, in addition to sampling the water from the bottom of the tank, was effective for delivering relatively gas nuclei-free water to the oxygenator. Increasing the concentration of oxygen within the fibers only slightly by application of a few bar therefore does not result in bubble growth, i.e., generation of a high hydrostatic pressure after enrichment of the water with oxygen is unnecessary.

A hydrostatic pressure of only 45 psi would be insufficient, of course, for perfusion of coronary arteries through the small channels available in angioplasty catheters. However, the relatively large bore tubing (approximately 0.5 mm i.d.) which was adequate to preserve the stability of the oxygen-supersaturated water allowed flow rates in the 30 to 100 cc/min range. Catheters with similar channels would be quite suitable for delivery of an oxygen-supersaturated cardioplegic solution into the aortic root during cardiopulmonary bypass procedures.

In a separate run, a similar Terumo hollow fiber oxygenator was enclosed in a stainless steel housing, so that much higher pressures could be tested. A SciMed membrane oxygenator may also be used. The arrangement for adjusting hydrostatic and oxygen gas pressures was similar to that noted above, but regulators which permitted a maximum pressure of about 500 psi were used. Hydrostatic pressure was maintained at about 20 to 50 psi greater than the oxygen gas pressure surrounding the bundle of fibers (i.e., the gas pressure inside the steel housing, external to the bundle).

Oxygen gas pressures of approximately 20 psi (to compare to the use of the oxygenator without the housing above) 150 psi, and 500 psi were tested. At 150 psi, no bubbles in the effluent were noted when silica fibers having an internal diameter of 150 microns or less were tested under tap water. However, at 500 psi, bubbles were noted in the effluent, even when a silica tubing with an i.d. of 50 microns was used.

The liquid output of the oxygenator was connected to an air-driven hydraulic pump (SC Hydraulics, Inc.). Hydrostatic pressure was increased to a range of about 0.7 kbar to 1.0 kbar within a T-tube mounted at the top of a 600 cc capacity high pressure vessel (High Pressure Equipment Corp.). The output from the T-tube was connected to a liquid regulator (Tescom), which allowed a reduction in pressure to a range of 4,000 psi or less. Following brief hydrostatic compression in the T-tube, the effluent, delivered at a pressure of about 3,000 to 4,000 psi through silica tubing having an i.d. of approximately 75 microns, was completely free of bubbles.

Thus, conventional oxygenators can be used to provide the high level of dissolved oxygen sought in clinical or industrial applications of gas-supersaturated liquids. At relatively low gas pressures, on the order of a few bar, application of additional hydrostatic pressure, after enrichment of the liquid with the gas, is unnecessary if the water is made relatively bubble-free by filtration and/or prolonged standing, as in the 3 runs performed at a gas pressure of about 20 psi. Much higher dissolved gas pressures still benefit from a further increase in hydrostatic pressure, as described in prior disclosures.

Experimental results have shown that the disclosed apparatus enables higher pressures to be safely achieved in order to produce a gas concentration exceeding two bar, both rapidly and continuously. Thus, the disclosed apparatus, in combination with a high resistance delivery system, allows the gas-enriched fluid to be injected into a one bar environment without bubble formation.

It will be apparent to those of ordinary skill in the art that the gas-liquid contacting region may embodied in an oxygenator or a membrane, or their equivalents. If a membrane oxygenator is used, a silicon membrane is preferred. Suitable oxygenators include those manufactured by Hoechst Celanese (LIQUI-CEL® CONTACTORS) and by Medtronic, (MAXIMA PLUS[198] OXYGENATOR) and their equivalents.

In addition to oxygen as a gas of choice, air can be used usefully in combination with water or gasoline, for example, to promote efficient combustion in an internal combustion engine. Water can be used in combination with carbon dioxide or nitrogen in certain industrial applications.

While the best mode for carrying out the invention has been described in detail, those familiar with the art to which this invention relates will recognize various alternative designs and embodiments for practicing the invention as defined by the following claims.

I claim:

1. An apparatus for delivering a high partial pressure of a gas into a liquid, comprising:

a gas transfer device having a housing including an upstream region, a downstream region, and a gas-liquid contacting region with contacting members located intermediate the upstream and downstream regions;

a liquid inlet port defined in the upstream region for receiving gas-depleted liquid;

a liquid outlet port defined in the downstream region for delivering gas-enriched liquid;

a gas inlet port defined in the housing for receiving the gas before contact with the liquid in the contacting region;

a gas outlet port defined in the housing for returning gas which is undissolved in the liquid;

a reservoir of gas for supplying the gas at a high pressure (P); and a flask of gas-depleted liquid in gaseous communication with the reservoir, the flask being in liquid communication with the liquid inlet port and in gaseous communication at a pressure (p), where p is less than P, with the gas inlet port of the gas transfer device;

whereby the reservoir of gas provides hydrostatic pressure for urging the liquid through the contacting members and the gas around the contacting members of the contacting region so that the gas does not diffuse across the members thereof.

2. The apparatus of claim 1 further comprising:

a first regulator located between the reservoir of gas and the flask of liquid.

3. The apparatus of claim 1 further comprising:

a second regulator situated between the flask of liquid and the gas inlet port of the gas transfer device.

4. The apparatus of claim 1 further comprising:

a first regulator located between the reservoir of gas and the flask of liquid; and a second regulator located between the flask of liquid and the gas transfer device.

5. The apparatus of claim 1 wherein the flask of gas-depleted liquid includes:

a liquid conduit having an open end located below a meniscus of liquid contained within the flask in order to promote delivery of a relatively bubble-free liquid to the liquid inlet port of the gas transfer device.

6. The apparatus of claim 1 further comprising:

a high resistance delivery channel in communication with the liquid outlet port, the high resistance delivery channel serving to supply a gas-enriched, bubble-free liquid to a desired site.

7. The apparatus of claim 1 wherein (P)-(p) is within a range of about 5 p.s.i. to about 20 p.s.i.

8. The apparatus of claim 1 wherein the gas comprises oxygen and the liquid comprises blood.

9. The apparatus of claim 1 wherein the gas comprises oxygen and the liquid comprises water.

10. The apparatus of claim 1 wherein the gas comprises air and the liquid comprises water.

11. The apparatus of claim 1 wherein the gas comprises air and the liquid comprises gasoline.

12. The apparatus of claim 1 wherein the gas comprises carbon dioxide and the liquid comprises water.

13. The apparatus of claim 1 wherein the gas comprises nitrogen and the liquid comprises water.

14. A method for delivering a high partial pressure of a gas into a liquid, comprising:

providing a gas transfer device having contacting members with a gas-liquid contacting region;

supplying a gas under pressure to a flask of gas-depleted liquid for expelling the liquid therefrom and to the gas transfer device;

ducting the gas-depleted liquid to the gas transfer device; and regulating a pressure differential within the contacting region between the gas-depleted liquid and the gas whereby the liquid is urged through the contacting members and the gas flows around the contacting members so that the gas does not bubble across the members.

* * * * *